United States Patent
Kadziauskas et al.

(10) Patent No.: US 7,182,759 B2
(45) Date of Patent: *Feb. 27, 2007

(54) CATARACT EXTRACTION APPARATUS AND METHOD WITH RAPID PULSE PHACO POWER

(75) Inventors: Kenneth E. Kadziauskas, Coto De Caza, CA (US); Mark E. Steen, Chino Hills, CA (US); Paul Rockley, Corona Del Mar, CA (US); James W. Staggs, Laguna Niguel, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/232,543

(22) Filed: Sep. 21, 2005

(65) Prior Publication Data

US 2006/0084961 A1   Apr. 20, 2006

Related U.S. Application Data

(63) Continuation of application No. 10/731,455, filed on Dec. 8, 2003, now Pat. No. 6,962,583, which is a continuation-in-part of application No. 09/949,405, filed on Sep. 7, 2001, now Pat. No. 6,733,491.

(51) Int. Cl.
*A61B 18/18*   (2006.01)
*A61B 18/20*   (2006.01)
*A61F 9/009*   (2006.01)

(52) U.S. Cl. ............ 606/6; 606/4; 606/10; 606/107; 604/22

(58) Field of Classification Search ........... 606/4–6, 606/10–12, 107, 127, 128, 167–171; 607/88, 607/89; 604/20–22, 28, 30; 600/398–402
See application file for complete search history.

(56) References Cited

U.S. PATENT DOCUMENTS

| | | | |
|---|---|---|---|
| 3,971,382 A | 7/1976 | Krasnov | |
| 3,982,541 A | 9/1976 | L'Esperance, Jr. | |
| 4,538,608 A | 9/1985 | L'Esperance, Jr. | |
| 4,744,360 A | 5/1988 | Bath | |
| 4,963,142 A | 10/1990 | Loertscher | |
| 5,057,098 A | 10/1991 | Zelman | |
| 5,074,861 A | 12/1991 | Schneider et al. | |
| 5,123,902 A | 6/1992 | Muller et al. | |
| 5,139,504 A | 8/1992 | Zelman | |
| 5,263,950 A | 11/1993 | L'Esperance, Jr. | |
| 5,403,307 A * | 4/1995 | Zelman | 606/6 |
| 5,651,783 A | 7/1997 | Reynard | |
| 5,695,461 A | 12/1997 | Schaible | |
| 5,700,240 A | 12/1997 | Barwick, Jr. et al. | |
| 5,738,677 A * | 4/1998 | Colvard et al. | 606/4 |
| 5,957,914 A | 9/1999 | Cook et al. | |

(Continued)

*Primary Examiner*—A. Farah
(74) *Attorney, Agent, or Firm*—Advanced Medical Optics, Inc.

(57) ABSTRACT

Apparatus for the removal of lens tissue includes a first handpiece having a laser emitting probe sized for insertion into a lens capsule and radiating a lens therein. The laser emitting probe includes a lumen for introducing irrigation fluid into the lens capsule. A second handpiece includes a pulsed controlled vibrated needle for insertion into the lens capsule and emulsifying laser eradiated lens tissue. The vibrated needle includes a lumen therethrough for aspiration of emulsified lens tissue and irrigation fluid.

10 Claims, 13 Drawing Sheets

U.S. PATENT DOCUMENTS

| | | |
|---|---|---|
| 6,013,049 A | 1/2000 | Rockley et al. |
| 6,083,193 A | 7/2000 | Kadziauskas et al. |
| 6,193,683 B1 | 2/2001 | Ludin et al. |
| 6,322,556 B1 | 11/2001 | Gwon et al. |
| 6,322,557 B1 | 11/2001 | Nikolaevich et al. |
| 6,325,792 B1 | 12/2001 | Swinger et al. |
| 6,328,732 B1 | 12/2001 | Donitzky et al. |
| 6,544,254 B1 | 4/2003 | Bath |
| 6,623,477 B1 | 9/2003 | Elbrecht et al. |
| 6,629,948 B2 | 10/2003 | Rockley et al. |
| 6,733,491 B2 * | 5/2004 | Kadziauskas et al. .......... 606/6 |
| 6,780,165 B2 | 8/2004 | Kadziauskas et al. |
| 6,830,555 B2 * | 12/2004 | Rockley et al. ................ 604/22 |
| 6,962,583 B2 * | 11/2005 | Kadziauskas et al. .......... 606/6 |
| 2002/0111608 A1 | 8/2002 | Baerveldt et al. |

* cited by examiner

CATARACT EXTRACTION APPARATUS AND METHOD WITH RAPID PULSE PHACO POWER

The present application is a continuation of U.S. patent application Ser. No. 10/731,455, filed Dec. 8, 2003, now U.S. Pat. No. 6,962,583, which is a continuation-in-part of U.S. application Ser. No. 09/949,405, filed Sep. 7, 2001, now U.S. Pat. No. 6,733,491.

The present invention generally relates to apparatus and method for extracting cataract tissue and more particularly is directed to combined use of vibrational and laser energy to effect cataract removal.

An eye generally includes an anterior chamber and a posterior chamber separated by a lens contained in a lens capsule. The lens functions to focus incoming light onto a retina disposed on a rear wall of the posterior chamber.

Cataracts cause the lens of an eye to become clouded, which interferes with proper transmission and focusing of light on the retina. A common practice to alleviate this condition is by surgically removing the cataractic lens and replacing it with an artificial intraocular lens.

Early lens removal was effected through manual extraction which required a wound of about 12 mm in length. This large opening can result in corneal or sclera tissue damage.

Externally applied laser radiation has been used to soften a cataract lens before manual extraction therefor. See U.S. Pat. Nos. 4,825,865, 5,057,098, 5,112,339, 5,139,504 and 5,403,307. Such manual extraction requires large entry wounds as hereinabove noted.

Phacoemulsification, on the other hand, enables the removal of a cataractic lens through a much smaller incision, for example between about 2.5 to about 4 mm. In this procedure, a needle is inserted through the incision into a lens capsule and the needle is ultrasonically vibrated to mechanically emulsify the lens. Once fragmented, or emulsified, the lens material is aspirated through a lumen through the phacoemulsification needle.

While emulsifying the lens and aspirating lens fragments, a simultaneous flow of irrigation fluid into the lens capsule is provided around the needle through an annulus established by a sleeve concentrically disposed over the needle. This flow of liquid into the eye is necessary to prevent collapse of the anterior chamber of the eye during aspiration. In addition, the irrigation fluid cools the needle in order to prevent any thermal damage of the corneal or scleral tissue. While the sleeve surrounding a phacoemulsification needle provides the important function of establishing an annulus for introducing irrigation fluid into the lens capsule and also enlarges the overall diameter of the sleeve needle for which an incision must be made.

In addition, when irrigation fluid is introduced proximate the emulsifying needle tip, the immediate area in front of the needle is roiled. This occurs because of the counter-current flow of fluid being aspirated by the needle itself and the irrigation fluid being introduced over the surface of the needle. Needle vibration causes a cloud of debris which is roiled by the incoming infusion fluid which lessons the physicians visual acuity of the end of the needle which can slow the procedure.

The present invention provides for the combined use of laser and vibrational energy to remove cataractic lens tissue and overcomes the drawbacks of a sleeved phacoemulsification needle. In addition, rapid pulsation of the vibratant needle is controlled to insure heat dissipation sufficient to present tissue damage.

SUMMARY OF THE INVENTION

Apparatus in accordance with the present invention for the removal of lens tissue generally includes a first handpiece including a laser emitting probe sized for insertion into a lens capsule and radiating lens tissue therein. In addition, the laser emitting probe includes a lumen for introducing an irrigation fluid into the lens capsule.

In combination therewith, a second handpiece is provided which includes a vibrated needle for insertion into the lens capsule and emulsifying lens tissue that has been softened, or fractured, by the laser radiation. The vibrated needle includes a lumen therethrough for aspiration of the emulsified lens tissue and irrigation fluid.

A power source is provided to provide pulsed electrical power to the second handpiece along with an input for enabling a surgeon to select an amplitude of the electrical pulses.

A control console is provided and interconnected with both first and second handpieces for controlling irrigation and aspiration rates and enabling simultaneous sequential operation of the laser emitting probe and the vibrated needle. In this manner, particularly hard or lens portions, that are resistant to emulsification, may be preconditioned for emulsification by laser radiation. The softening of lens tissue by laser is well known as set forth in the hereinabove referenced U.S. Patents.

In addition, the control console is structured and functions in response to the selected pulse amplitude for controlling a pulse duty cycle of power supplied to the second handpiece, an off duty cycle being controlled to ensure heat dissipation before a subsequent pulse is activated.

Because irrigation fluid is not simultaneously introduced proximate the vibrating needle, as is the case in prior art devices, no disturbance or churning of fluid occur which may provide for a "milky cloud" at the end of the needle which can tend to lessen visual acuity, which in turn, may interfere with the accuracy of the phacoemulsification by a physician.

Preferably the second handpiece includes a transducer for driving the vibrating needle at ultrasonic frequencies and the laser emitting probe comprises fiber optics with a irrigation lumen therethrough.

A method in accordance with the present invention for removing lens tissue from a lens capsule generally includes the steps of inserting a laser emitting probe having an irrigation lumen into the lens capsule along with a vibratable needle having an aspiration lumen.

Irrigation fluid is introduced into the lens capsule and the lens is softened or fractured by exposure to laser energy from the laser emitting probe.

The needle is vibrated to emulsify the lens tissue which is thereafter aspirated along with the irrigation fluid through an aspiration lumen in the vibratable needle. A pulse duty cycle provided to the needle is controlled in response to a selected pulse amplitude to provide an off duty cycle enabling heat dissipation before a subsequent pulse is activated.

The lens tissue may be exposed to laser radiation and emulsified simultaneously or the laser exposure may be intermittent and in a sequential manner. That is, the tissue may first be repeatedly exposed to laser radiation and thereafter emulsified.

BRIEF DESCRIPTION OF THE DRAWING

The advantages and features of the present invention will be better understood by the following description when considered in conjunction with the accompanying drawing in which.

DETAILED DESCRIPTION

Figure 1:
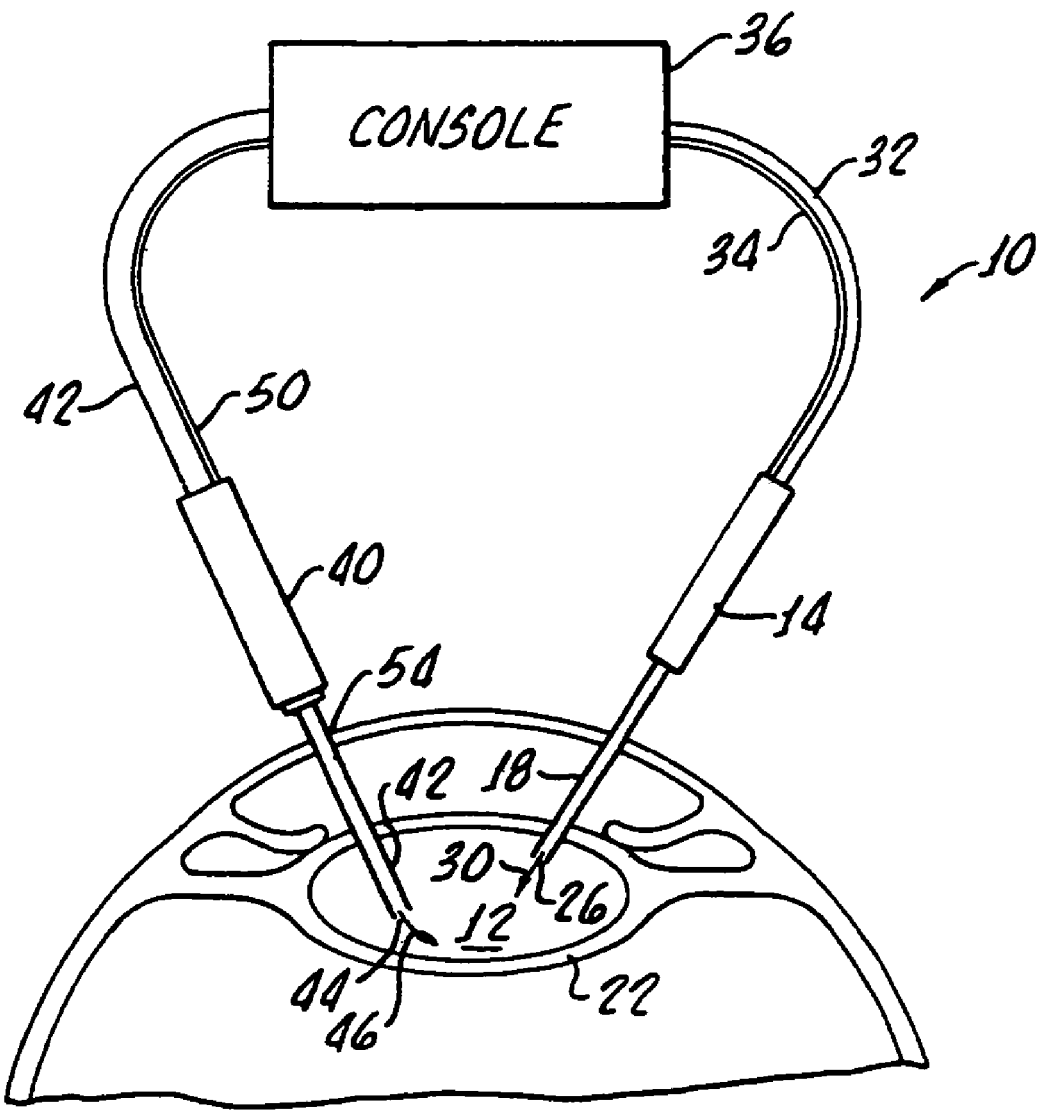
FIG. 1 is a diagram of apparatus in accordance with the present invention generally showing a first handpiece for inserting a laser emitting probe into a lens capsule along with introducing an irrigation fluid into the lens capsule along with a second handpiece for inserting a vibratable needle into the lens capsule for emulsification of lens tissue and aspiration of emulsified tissue and irrigation fluid.

With reference to FIG. 1 there is shown apparatus 10 for the removal of lens tissue 12. The apparatus 10 generally includes a first handpiece 14 which includes a laser emitting probe 18 for insertion into a lens capsule 22 for radiating the lens tissue 12. The handpiece 14 may include any suitable laser, such as, a Er:YAG laser for providing laser energy to the probe 18 which includes fiber optics for transmitting the laser energy into the lens capsule 22 and lens 12.

A lumen 26 through the probe 18 is provided for introducing an irrigation fluid, indicated by the arrow 30, into the lens capsule 22. Power and irrigation fluid are provided to the handpiece 14 through lines 32, 34 connected to a control console 36. The control counsel 36 may be of any suitable type, such as for example, one manufactured by Allergan, Inc. under the trade name Sovereign®.

A second handpiece 40 includes a vibrated needle 42 for emulsifying lens tissue 12. Any suitable handpiece may be utilized, such as for example, one sold by Allergan, Inc. under the trade name Sovereign®. The handpiece 40 is interconnected to the console 36 and controlled thereby through a power line 42. A lumen 44 through the needle 42 is provided for aspiration of emulsified lens tissue 12 and irrigation fluid as indicated by the arrow 46. Vacuum is provided by the console through an aspiration line 50 interconnecting the handpiece 40, needle lumen 44 to the console 36.

In operation, the laser emitting probe is utilized to soften, or fracture selected portion of the lens which are thereafter emulsified by the needle 42 and aspirated through the lumen 44 and line 50. The laser probe 18 and emulsifying needle 42 may be operated simultaneously to effect lens removal or in a sequential manner in which the lens 12 is preferably radiated by laser light and thereafter emulsified by the vibrating needle 42.

It should also be noted that since the needle 42 does not include a conventional sleeve (not shown) a smaller incision or wound 54 is enabled. The wound size may be a small as 1.25 mm which is to be compared with conventional sleeve needle (not shown) which require a slit or wound opening (not shown) of about 2½ to 3 mm.

A combined use of the laser emitting probe 18 emulsifying needle 42 increases the efficiency of lens removal, and is particularly useful in cases in which the lens is of sufficient hardness such that laser energy alone would not efficiently extract the cataract.

The laser, in combination with ultrasonic energy, would result in a lower total energy required to extract the cataract. This may also reduce the likelihood of adverse events such as would burns. In addition, smaller incisions may be used for cataract extraction.

Figure 2:
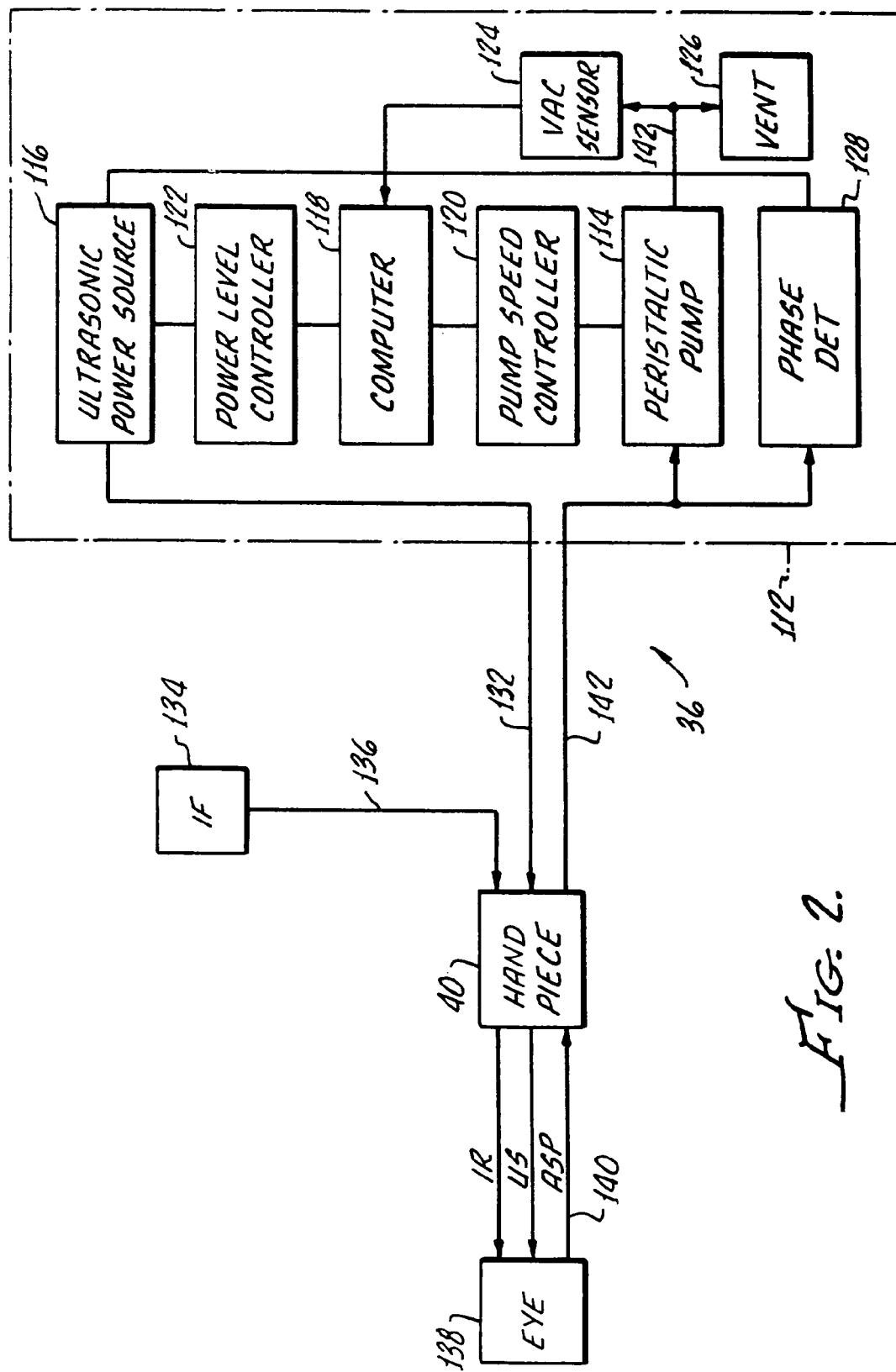
FIG. 2 is a functional block diagram of a control system for the second handpiece in accordance with the present invention.
Figure 3:
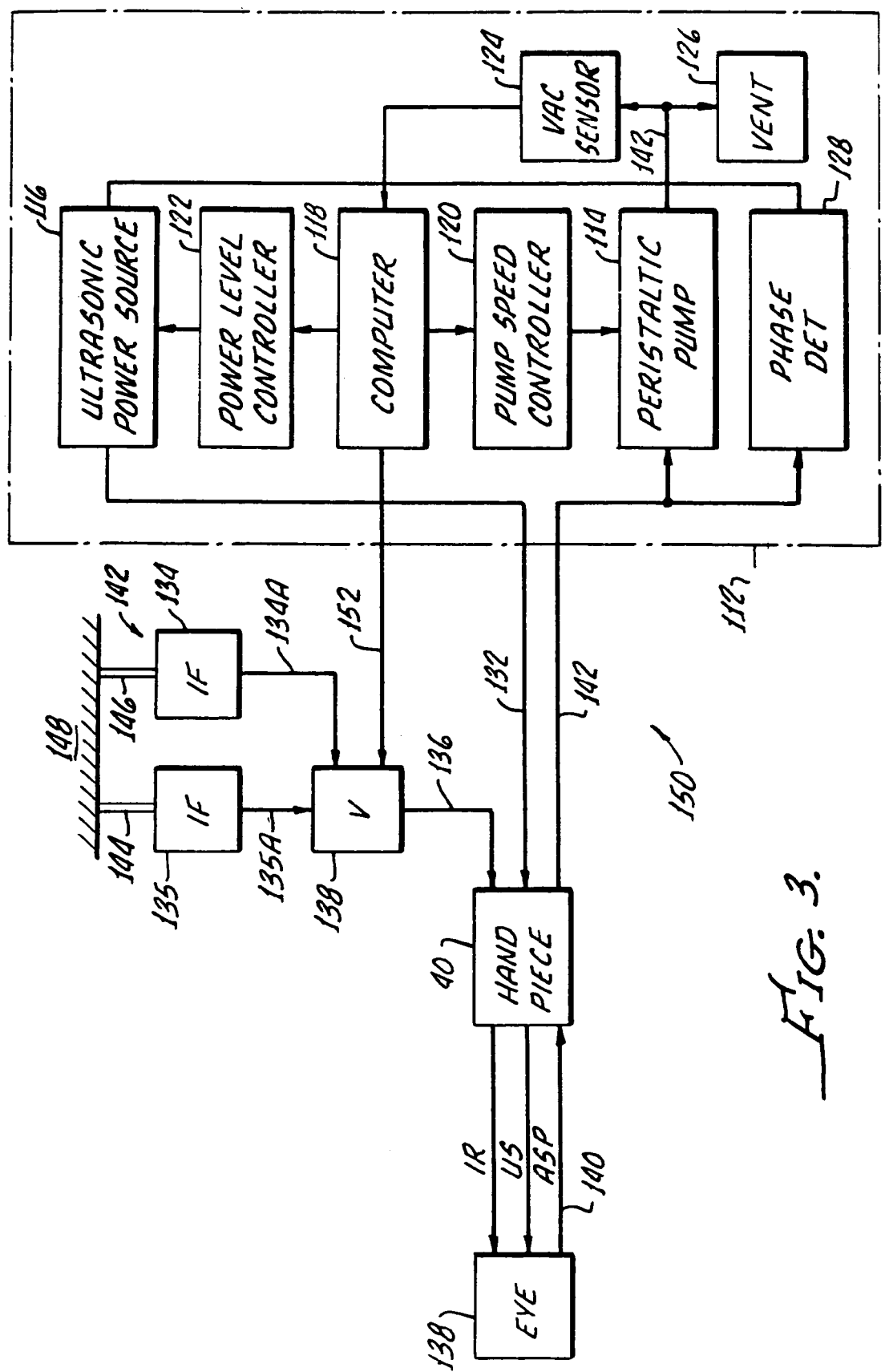
FIG. 3 is a functional block diagram of an alternative embodiment of a phacoemulsification system in accordance with the present invention which includes apparatus for providing irrigation fluid at more than one pressure to a handpiece.
Figure 4:
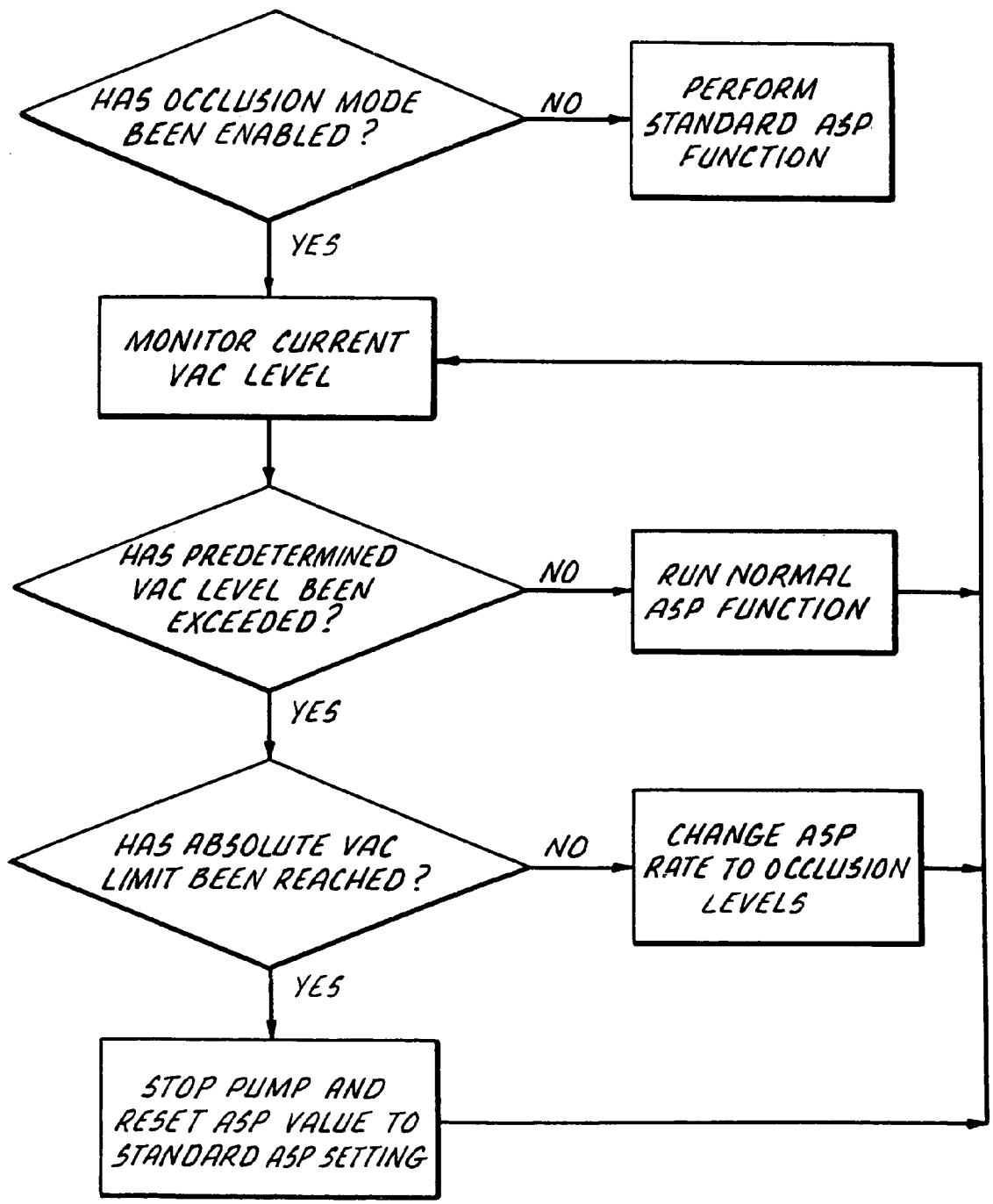
FIG. 4 is a flow chart illustrating the operation of the occluded-unoccluded mode of the phacoemulsification system with variable aspiration rates.

Turning now to FIGS. 2–4, and particularly to FIG. 2 thereof, there is shown, in functional block diagram form, the control system or console 36. The system has a control unit 112, indicated by the dashed lines in FIG. 1 which includes a variable speed peristaltic pump 114, which provides a vacuum source, a source of pulsed ultrasonic power 116, and a microprocessor computer 118 that provides control outputs to pump speed controller 120 and ultrasonic power level controller 122. A vacuum sensor 124 provides an input to computer 118 representing the vacuum level on the output side of peristaltic pump 114. Suitable venting is provided by vent 126.

As hereinafter described in greater detail, a phase detector 128 provides an input to computer 118 representing a phase shift between a sine wave representation of the voltage applied to the record 40 and the resultant current into the handpiece 40. The block representation of the handpiece 40 includes the needle 42 and a piezoelectric crystal (not shown), for ultrasonically vibrating the needle.

The control unit 112 supplied ultrasonic power on line 132 to the phacoemulsification handpiece 40 and needle 42. An irrigation fluid source 134 is fluidly coupled to handpiece 40 and needle 42 through line 136. The irrigation fluid and ultrasonic power are applied by handpiece 40 to a patient's eye which is indicated diagrammatically by block 138.

Aspiration of the eye 138 is achieved by means of the control unit peristaltic pump 114 through lines 140 and 142.

A switch 143 disposed on the handpiece 40 may be utilized as a means for enabling a surgeon to select an amplitude of electrical pulses to the handpiece via the computer 118, power level controller 122 and ultrasonic power source 116 as hereinafter discussed. It should be appreciated that any suitable input means, such as, for example, a foot pedal (not shown) may be utilized in lieu of the switch 143.

The computer 118 responds to preset vacuum levels in output line 142 from peristaltic pump 114 by means of signals from the previously mentioned vacuum sensor 124. Operation of the control unit in response to the occluded-unoccluded condition of handpiece 40 is shown in the flow diagram of FIG. 4.

As shown in FIG. 4, if the handpiece aspiration line 140 is occluded, the vacuum level sensed by vacuum sensor 124 will increase. The computer 118 has operator-settable limits for aspiration rates, vacuum levels and ultrasonic power levels. As illustrated in FIG. 4, when the vacuum level sensed by vacuum sensor 124 reaches a predetermined level as a result of occlusion of the handpiece aspiration line 140, computer 118 instructs pump speed controller 120 to change the speed of the peristaltic pump 114 which, in turn, changes the aspiration rate.

It will be appreciated that, depending upon the characteristics of the material occluding handpiece 40, the speed of the peristaltic pump 114 can either be increased or decreased. When the occluding material is broken up, the vacuum sensor 124 registers a drop in vacuum level, causing computer 118 to change the speed of peristaltic pump 114 to an unoccluded operating speed.

Figure 5:
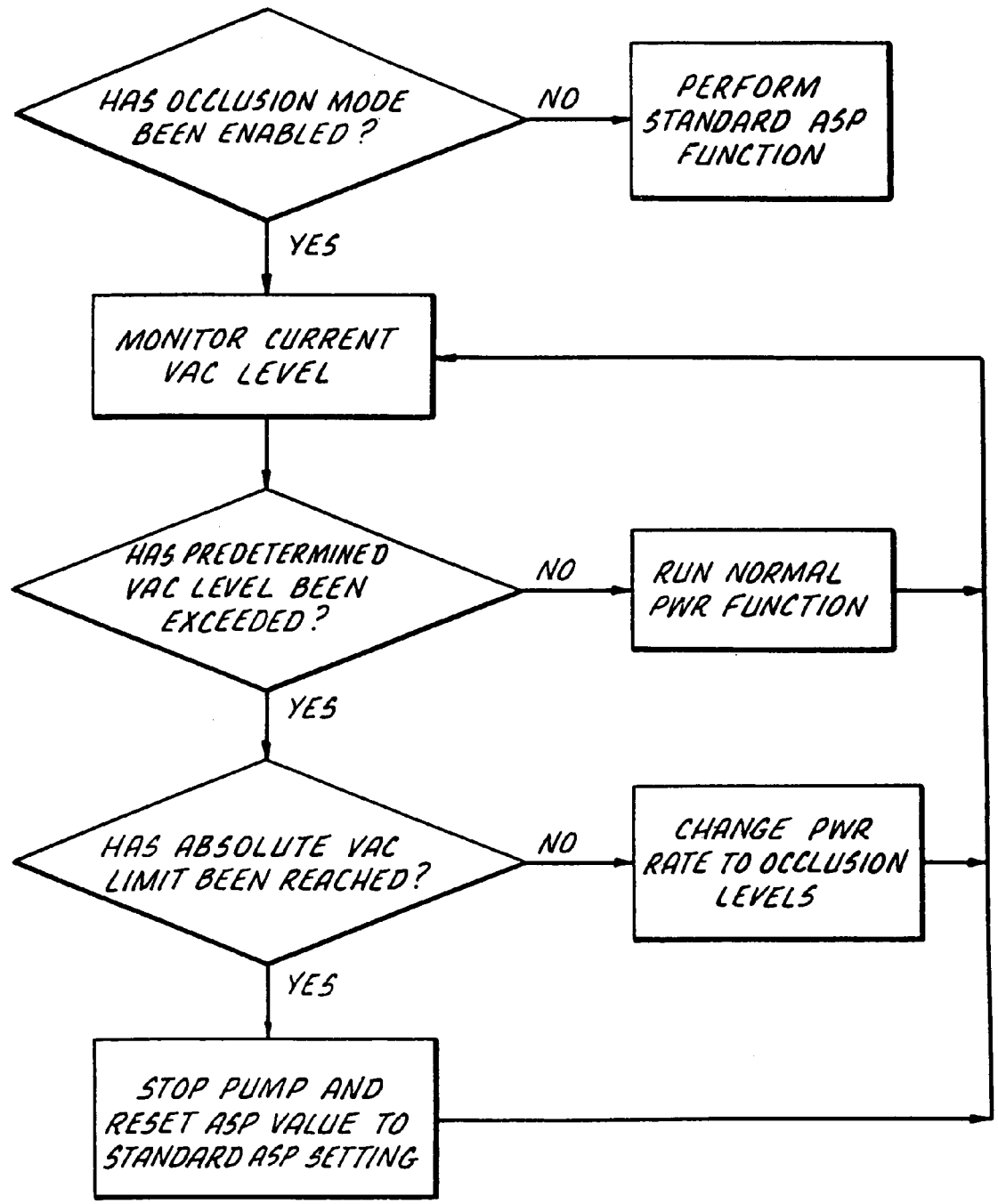
FIG. 5 is a flow chart illustrating the operation of the occluded-unoccluded mode of the phacoemulsification system with variable ultrasonic power levels.

In addition to changing the phacoemulsification parameter of aspiration rate by varying the speed of the peristaltic pump 114, the power level of the ultrasonic power source 16 can be varied as a function of the occluded or unoccluded condition of handpiece 40. FIG. 5 illustrates in flow diagram form the control of the ultrasonic power source power level by means of computer 18 and power level controller 122. It will be appreciated that the flow diagram of FIG. 5 corresponds to the flow diagram of FIG. 4 but varies the phacoemulsification parameter of the ultrasonic power level.

Figure 6:
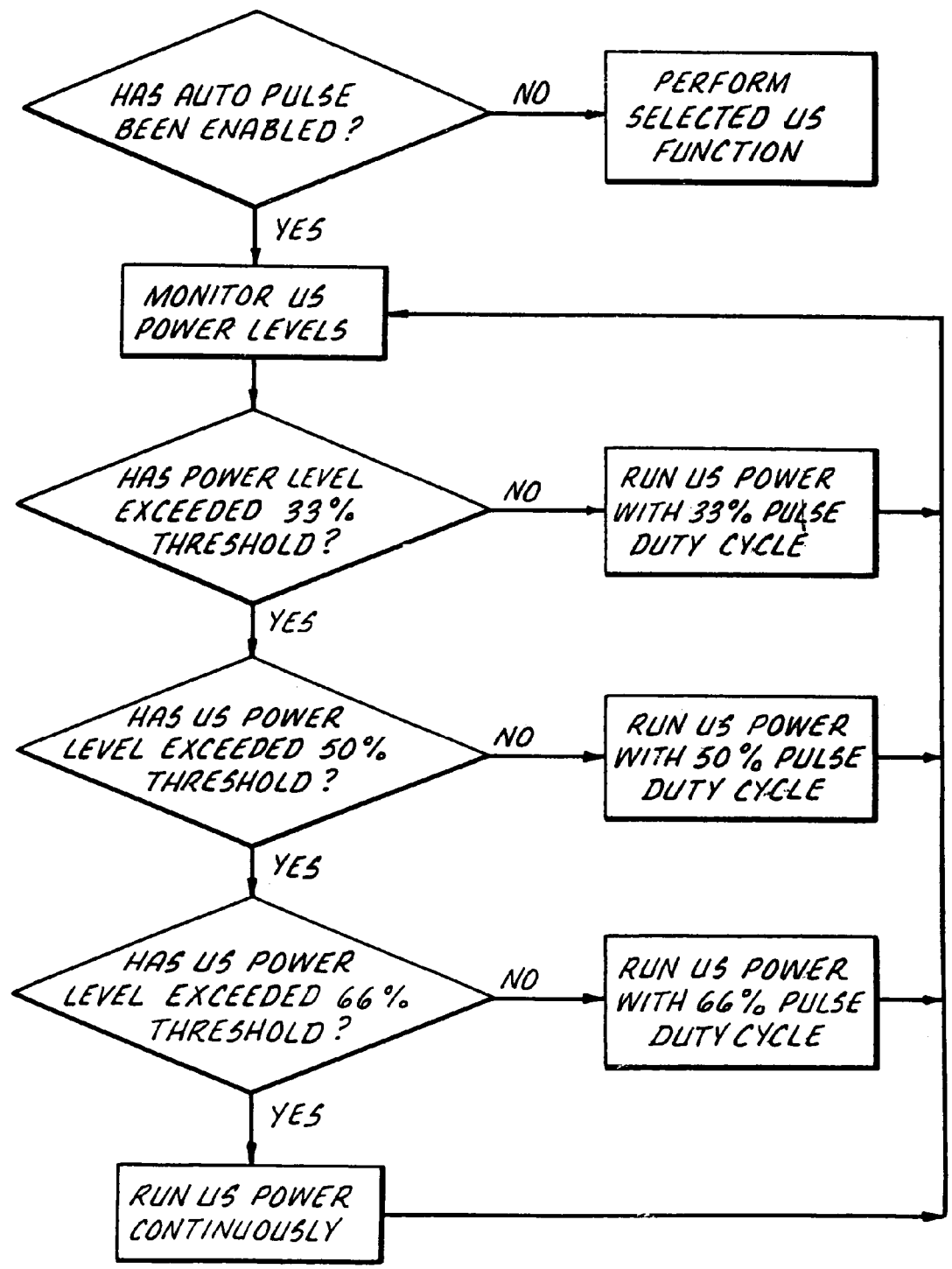
FIG. 6 is a flow chart illustrating the operation of the variable duty cycle pulse function of the phacoemulsification system.

With reference to FIG. 6, there is shown a flow diagram depicting the control of the ultrasonic power source 116 to produce varying pulse duty cycles as a function of selected power levels. As shown in FIG. 6, and by way of illustration only, a 33% pulse duty cycle is run until the power level exceeds a preset threshold; in this case, 33%. At that point, the pulse duty cycle is increased to 50% until the ultrasonic power level exceeds a 50% threshold, at which point the pulse duty cycle is increased to 66%. When the ultrasonic power level exceeds 66% threshold, the power source is run continuously, i.e., a 100% duty cycle. Although the percentages of 33%, 50% and 66% have been illustrated in FIG. 6, it should be understood that other percentage levels can be selected to define different duty cycle shift points.

Figure 14:
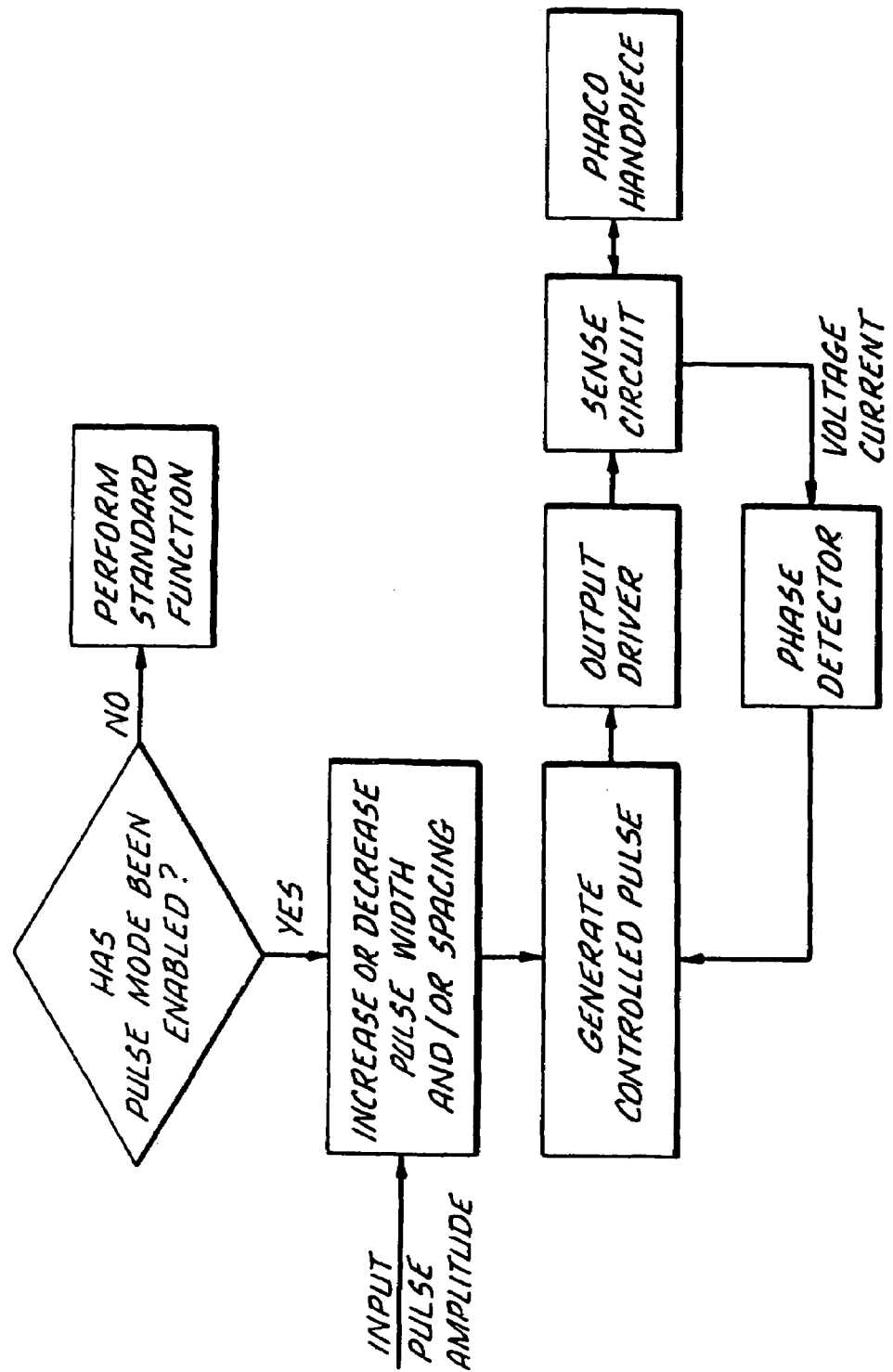
FIG. 14 is a function block control diagram of a pulse control phacoemulsification system.

With reference to FIG. 14, when the computer 118 has been enabled for pulse mode operation by an amplitude input via the switch 143, the use of thermal tissue damage is reduced. In accordance with the present invention, very rapid pulse duration is provided with adequate energy to cut the tissue with kinetic or mechanical energy but then the pulse is turned off long enough to eliminate the thermal BTU's before the next pulse is activated. A surgeon may vary the pulse amplitude in a linear manner via the switch 143 and the control unit in response to the selected pulse amplitude, irrigation and aspiration fluid flow rates, controlling a pulse duty cycle. As hereinabove noted, an off duty duration or cycle is provided to ensure heat dissipation before a subsequent pulse is activated. In this way, increase amplitude will increase tip acceleration and thus BTU's for tissue damaging heat generation. That is, the surgeon can use. linear -power control to select the correct acceleration necessary to cut through the tissue density while the control unit provides a corresponding variation in pulse width and "Off time" to prevent tissue de-compensation from heat. The control unit is programmed depending on the phaco handpiece chosen (total wattage) or the phaco tip (dimensions, weight). This use of rapid pulsing is similar to how lasers operate with very short duration pulses. Pulses may have a repetition rate of between about 25 and 2000 pulses per second.

Turning back to FIG. 3, there is shown an alternative embodiment 150 of a phacoemulsification system, in accordance with the present invention, and which incorporates all of the elements of the system 110 shown in FIG. 2, with identical reference characters identifying components, as shown in FIG. 2.

In addition to the irrigation fluid source 134, a second irrigation fluid source 135 is provided with the sources 134, 135 being connected to the line 136 entering the handpiece/needle 130 through lines 134a, 135a, respectively, and to a valve 138. The valve 138 functions to alternatively connect line 134a and source 134 and line 135a and source 135 with the handpiece/needle 130 in response to a signal from the power level controller 122 through a line 152.

As shown, irrigation fluid sources 134, 135 are disposed at different heights above the handpiece 40 providing a means for introducing irrigation fluid to the handpiece 40 at a plurality of pressures, the head of the fluid in the container 135 being greater than the head of fluid in the container 134. A harness 142, including lines 144, 146 of different lengths when connected to the support 148, provides a means for disposing the containers 134, 135 at different heights over the handpiece 40.

The use of containers for irrigation fluids at the various heights is representative of the means for providing irrigation fluids at different pressures, and alternatively, separate pumps may be provided with, for example, separate circulation loops (not shown) which also can provide irrigation fluid at discrete pressures to the handpiece 40 upon a command from the power controller 122.

With reference to FIG. 6, if the handpiece 40 aspiration line 138 is occluded, the vacuum level sensed by the vacuum sensor 124 will increase. The computer 118 has operator-settable limits for controlling which of the irrigation fluid supplies 132, 133 will be connected to the handpiece 40. It should be appreciated that while two irrigation fluid sources, or containers 132, 133 are shown, any number of containers may be utilized.

Figure 7:
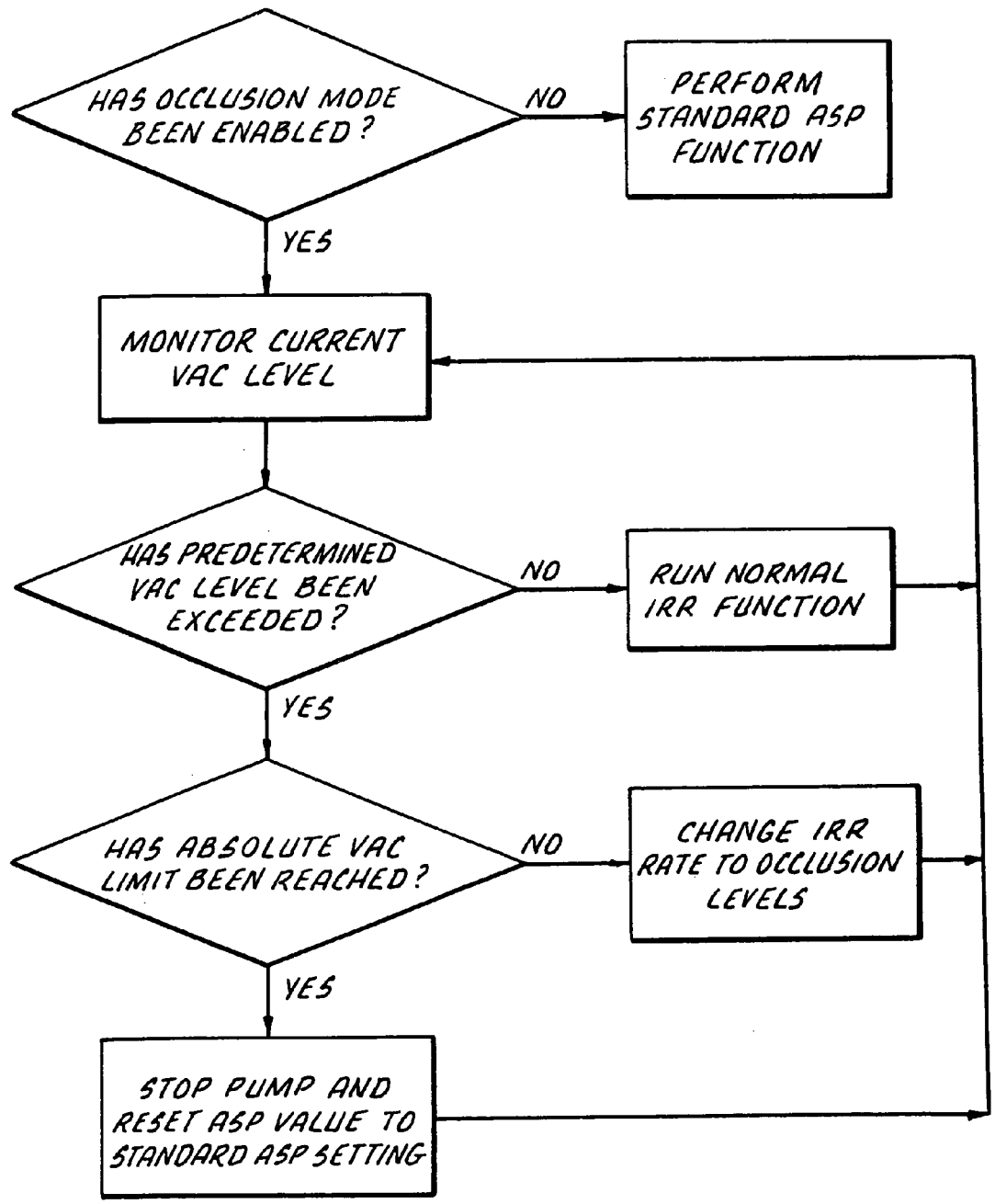
FIG. 7 is a flow chart illustrating the operation of the occluded-unoccluded mode of the phacoemulsification system with variable irrigation rates.

As shown in FIG. 7, when the vacuum level by the vacuum sensor 124 reaches a predetermined level, as a result of occlusion of the aspiration handpiece line 138, the computer controls the valve 138 causing the valve to control fluid communication between each of the containers 134, 135 and the handpiece/needle 130.

It should be appreciated that, depending upon the characteristics of the material occluding the handpiece 40, as hereinabove described and the needs and techniques of the physician, the pressure of irrigation fluid provided the handpiece may be increased or decreased. As occluded material 124, the vacuum sensor 124 registers a drop in the vacuum level causing the valve 138 to switch to a container 134, 135, providing pressure at an unoccluded level.

As noted hereinabove, it should be appreciated that more than one container may be utilized in the present invention, as an additional example, three containers (not shown) with the valve interconnecting to select irrigation fluid from any of the three containers, as hereinabove described in connection with the FIG. 2A container system.

In addition to changing phacoemulsification handpiece 40 parameter as a function of vacuum, the occluded or unoccluded state of the handpiece can be determined based on a change in load sensed by a handpiece/needle by way of a change in phase shift or shape of the phase curve.

Figure 8:
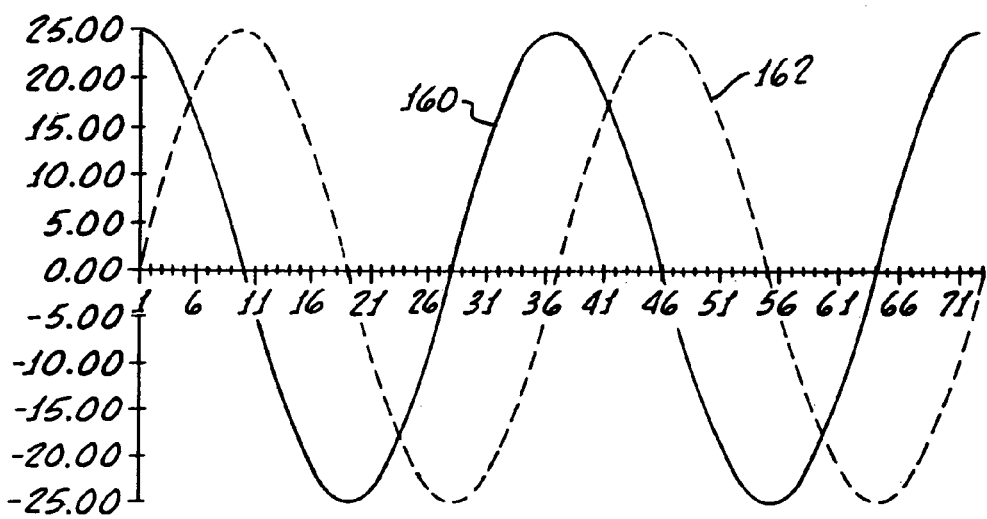
FIG. 8 is a plot of the 90 degree phase shift between the sine wave representation of the voltage applied to a piezoelectric phacoemulsification handpiece and the resultant current into the handpiece.

The typical range of frequencies used for phacoemulsification handpiece 40 is between about 30 kHz and about 50 kHz. When the frequency applied to the handpiece is significantly higher, or lower than resonancy, it responds electrically as a capacitor. The representation of this dynamic state is shown in FIG. 8 in which curve 160 (solid line) represents a sine wave corresponding to handpiece 40 current and curve 162 (broken line) represents a sine wave corresponding to handpiece 40 voltage.

Figure 9:
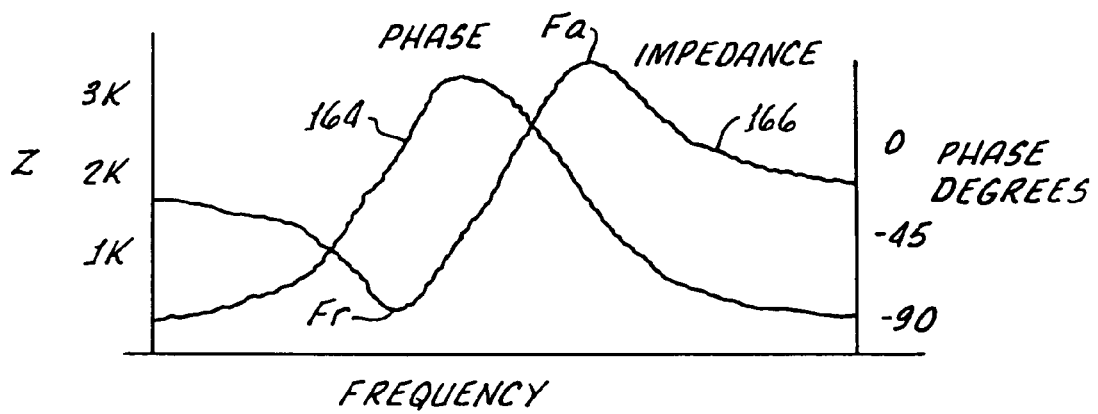
FIG. 9 is a plot of the phase relationship and the impedance of a typical piezoelectric phacoemulsification handpiece.

The impedance of the typical phacoemulsification handpiece 40 varies with frequency, i.e., it is reactive. The dependence of typical handpiece 40 phase and impedance as a function of frequency is shown in FIG. 9 in which curve 164 represents the phase difference between current and voltage of the handpieces function frequency and curve 166 shows the change in impedance of the handpiece as a function of frequency. The impedance exhibits a low at "Fr" and a high "Fa" for a typical range of frequencies.

Automatic tuning of the handpiece, as hereinabove briefly noted, is typically accomplished by monitoring the handpiece electrical signals and adjusting the frequency to maintain a consistency with selected parameters.

In order to compensate for a load occurring at the tip of the phacoemulsification handpiece, the drive voltage to the handpiece can be increased while the load is detected and then decreased when the load is removed. This phase detector is typically part of the controller in this type of system.

In such conventional phase detectors, the typical output is a voltage as proportional to the difference in alignment of the voltage and the current waveform, for example, −90 degrees as shown in FIG. 8. As shown in FIG. 9, it is important to consider that during the use of the handpiece, the waveform is varying in phase and correspondingly the output waveform is also varying.

Heretofore, the standard technique for measuring electrical phase has been to read a voltage that is proportional to phase and also to frequency. This type of circuit can be calibrated for use with a single frequency as changing the frequency would cause the calibration data to be incorrect.

This can also be seen with single frequency systems. The corrected phase value will draft due to variation in the circuit parameters.

The other typical approach is to utilize a microprocessor to compare the value of the phase detector output with that of a frequency detector and compute the true phase. This approach is fairly complex and is subject to drift of the individual circuits as well as-resolution limitations.

Figure 10:
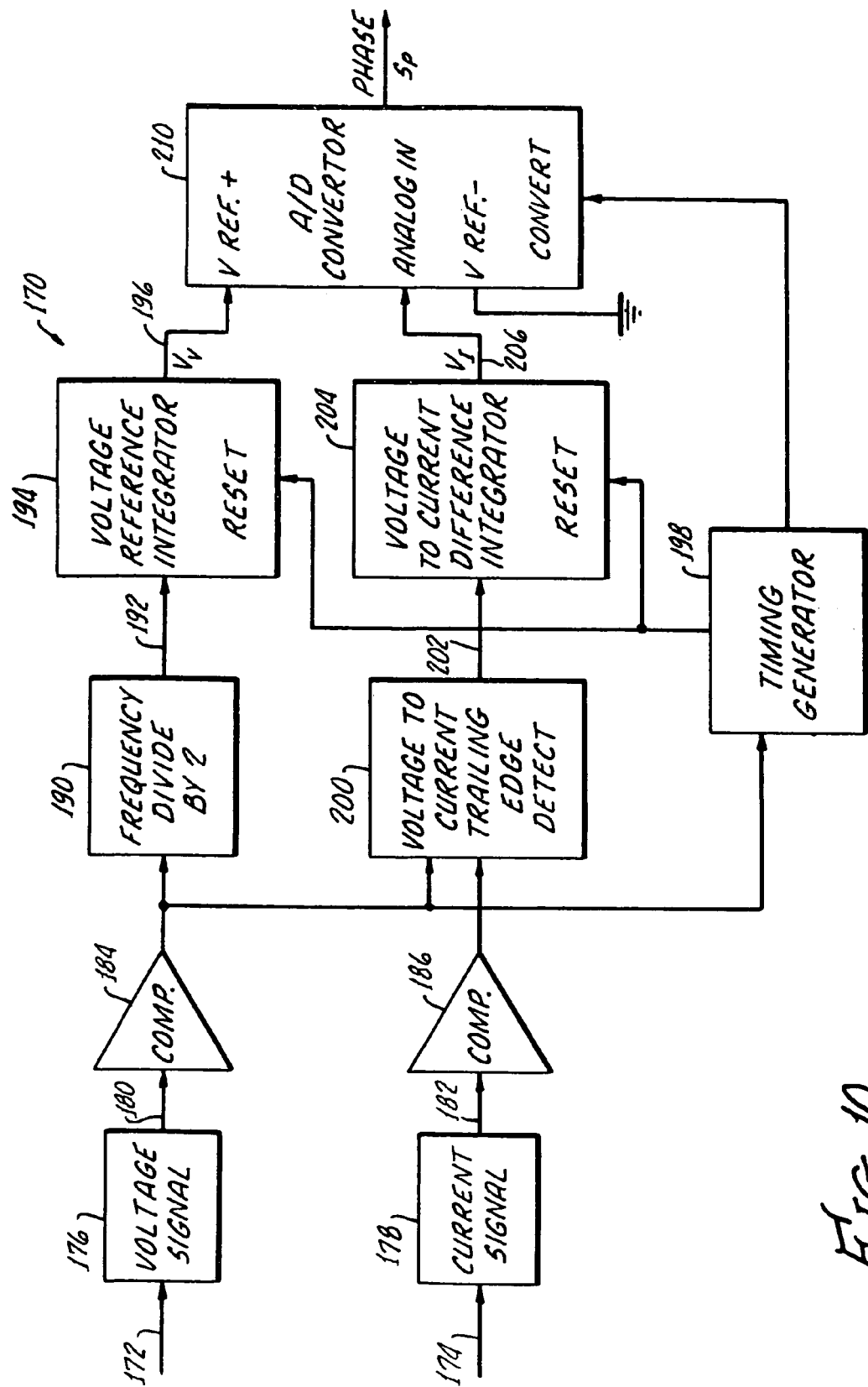
FIG. 10 is a block diagram of improved phase detector circuitry suitable for performing a method in accordance with the present invention.

A block diagram 170 as shown in FIG. 10 is representative of an improved phase detector suitable for performing the method in accordance with the present invention. Each of the function blocks shown comprises conventional state-of-the-art circuitry of typical design and components for producing the function represented by each block as hereinafter described.

The voltage input 172 and current 174 from a phacoemulsification handpiece 40 is converted to an appropriate signal using an attenuator 176 on the voltage signal to the phacoemulsification handpiece, and a current sense resistor 178 and fixed gain amplifier for the handpiece 40 current.

Thereafter, an AC voltage signal 180 and AC current signal 182 is passed to comparators 184, 186 which convert the analog representations of the phacoemulsification voltage and current to logic level clock signals.

The output from the comparator 184 is fed into a D flip flop integrated circuit 190 configured as a frequency divide by 2. The output 192 of the integrated circuit 190 is fed into an operational amplifier configured as an integrator 194. The output 196 of the integrator 194 is a sawtooth waveform of which the final amplitude is inversely proportional to the handpiece frequency. A timing generator 198 uses a clock synchronous with the voltage signal to generate A/D converter timing, as well as timing to reset the integrators at the end of each cycle.

This signal is fed into the voltage reference of an A/D converter via line 196.

The voltage leading edge to current trailing edge detector 200 uses a D flip flop integrated circuit in order to isolate the leading edge of the handpiece voltage signal. This signal is used as the initiation signal to start the timing process between the handpiece 40 voltage and handpiece 40 current.

The output 102 of the leading detector 200 is a pulse that is proportional to the time difference in occurrence of the leading edge of the handpiece 40 voltage waveform and the falling edge of the handpiece current waveform.

Another integrator circuit 204 is used for the handpiece phase signal 202 taken from the detector 200. The output 206 of the integrator circuit 204 is a sawtooth waveform in which the peak amplitude is proportional to the time difference in the onset of leading edge of the phacoemulsification voltage and the trailing edge of the onset of the handpiece current waveform. The output 206 of the integrator circuit 204 is fed into the analog input or an A/D (analog to digital converter) integrated circuit 210.

Therefore, the positive reference input 196 to the A/D converter 210 is a voltage that is inversely proportional to the frequency of operation. The phase voltage signal 196 is proportional to the phase difference between the leading edge of the voltage onset, and the trailing edge of the current onset, as well as inversely proportional to the frequency of operation. In this configuration, the two signals Frequency voltage reference 196 and phase voltage 146 track each other over the range of frequencies, so that the output of the A/D converter 210 produces the phase independent of the frequency of operation.

The advantage of utilizing this approach is that the system computer 118 (see FIGS. 1 and 2) is provided with a real time digital phase signal that 0 to 255 counts will consistently represent 0 to 359 degrees of phase.

The significant advantage is that no form of calibration is necessary since the measurements are consistent despite the frequencies utilized.

For example, using AMPs operation frequencies of 38 kHz and 47 kHz and integrator having a rise time of $150 \times 10^3$ V/2 and an 8 bit A/D converter having 256 counts, a constant ratio is maintained and variation in frequency does not affect the results. This is shown in the following examples.

EXAMPLE 1

38 KHz Operation

Period of 1 clock cycle=1/F@38 KHz=$26.32 \times 10^{-6}$ S
Portion of one period for I =90 degrees=$26.32 \times 10^{-6}$ S/4=$6.59 \times 10^{-6}$ S
Integrator output for one reference cycle =$(150 \times 10^{-3}$ V/S)×$(26.32 \times 10^{-6}$ S)=3.95 Volts
Integrator output from 90 degree cycle duration =$(150) \times 10^3$ V/S)×$(6.59 \times 10^{-6}$ S)=0.988 Volts
Resulting Numerical count from A/D converter =3.95 Volts/ 256 counts=0.0154 Volts per count
Actual Number of A/C counts for 90 degrees at 38 KHz

EXAMPLE 2

47 KHz Operation

Figure 11:
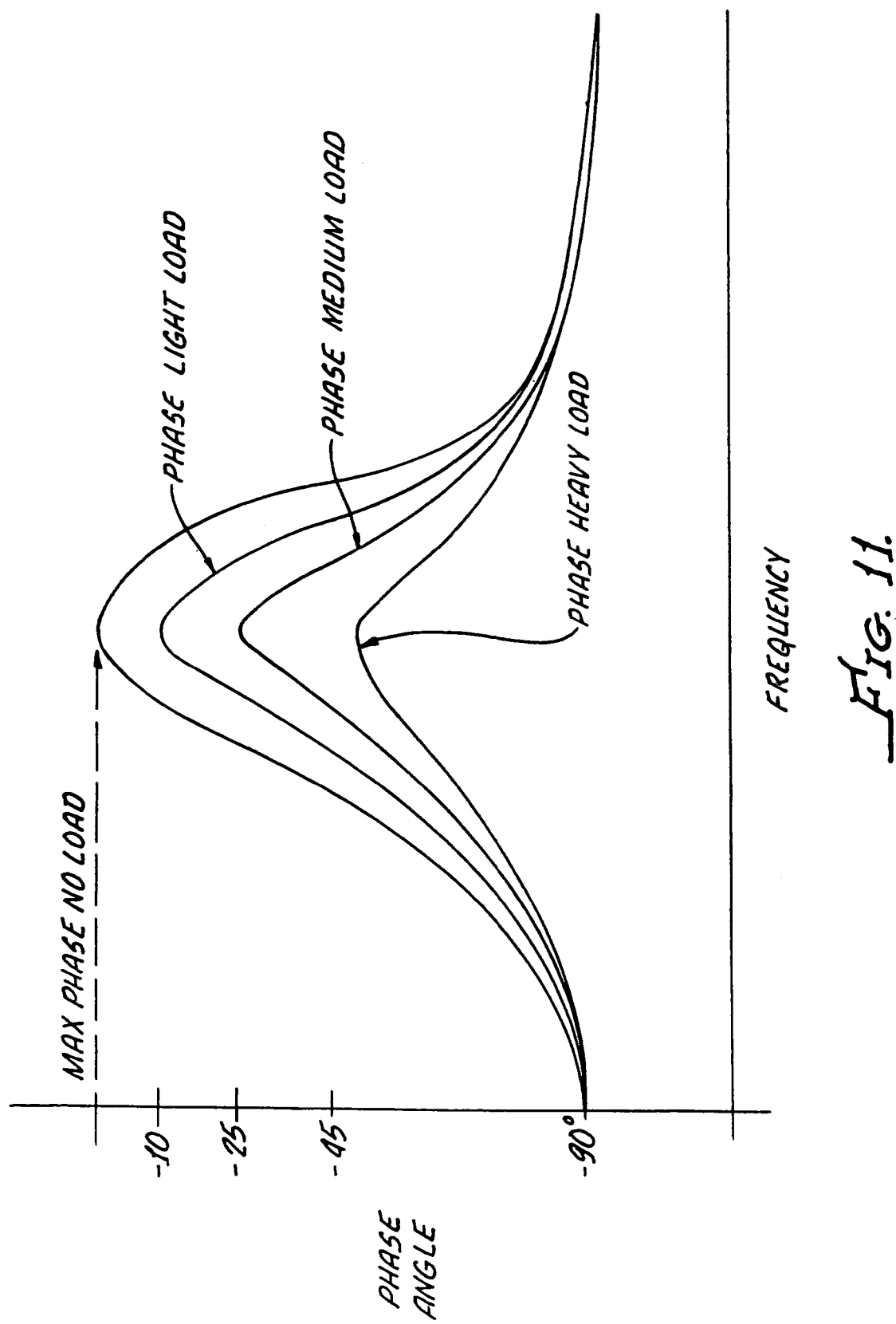
FIG. 11 is a plot of phase relationship as a function of frequency for various handpiece/needle loading.

Period of 1 clock cycle-1/F@47 KHz=$21.28 \times 10^{-6}$ S
Integrator output for one reference cycle =$(150 \times 10^3$ V/S)×$(21.28 \times 10^{-6}$ S)=3.19 Volts
Integrator output from 90 degree cycle duration =$(150 \times 10^3$ V/S)×$(5.32 \times 1010^{-6}$ S)=0.798 Volts
Resulting Numerical count from A/D converter =3.19 Volts/ 256 counts=0.0124 Volts per count
Actual Number of A/D counts for 90 degrees at 47 KHz = 0.798/0.0124=64 counts A plot of phase angle as a function of frequency is shown in FIG. 11 for various handpiece 40 loading, a no load (max phase), light load, medium load and heavy load.

Figure 12:
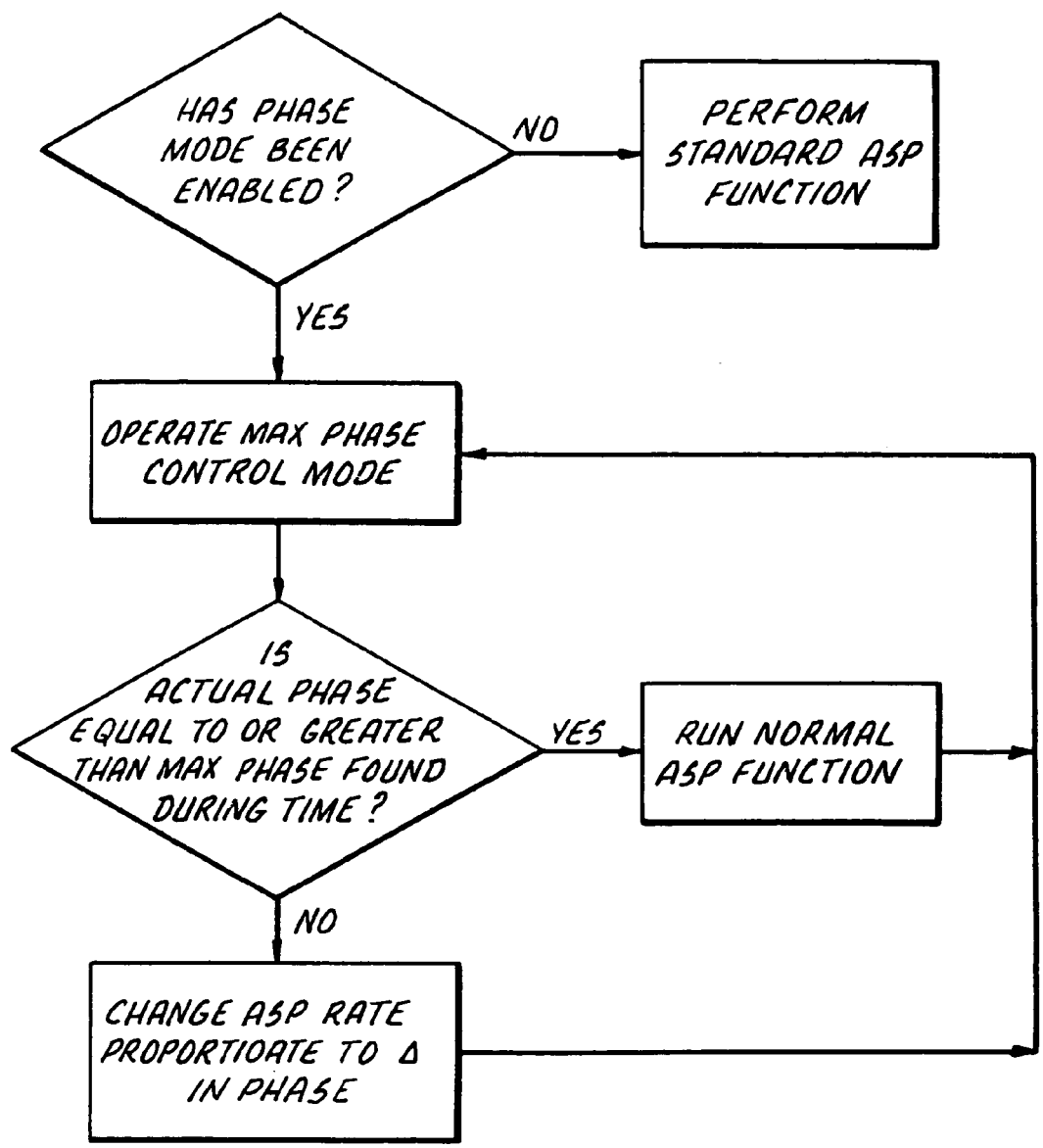
FIG. 12 is a function block diagram of a phase control phacoemulsification system utilizing phase angles to control handpiece/needle parameters with max phase mode operation.

With reference to FIG. 12, representing max phase mode operation, the actual phase is determined and compared to the max phase. If the actual phase is equal to, or greater than, the max phase, normal aspiration function is performed. If the actual phase is less than the max phase, the aspiration rate is changed, with the change being proportionate to the change in phase.

Figure 13:
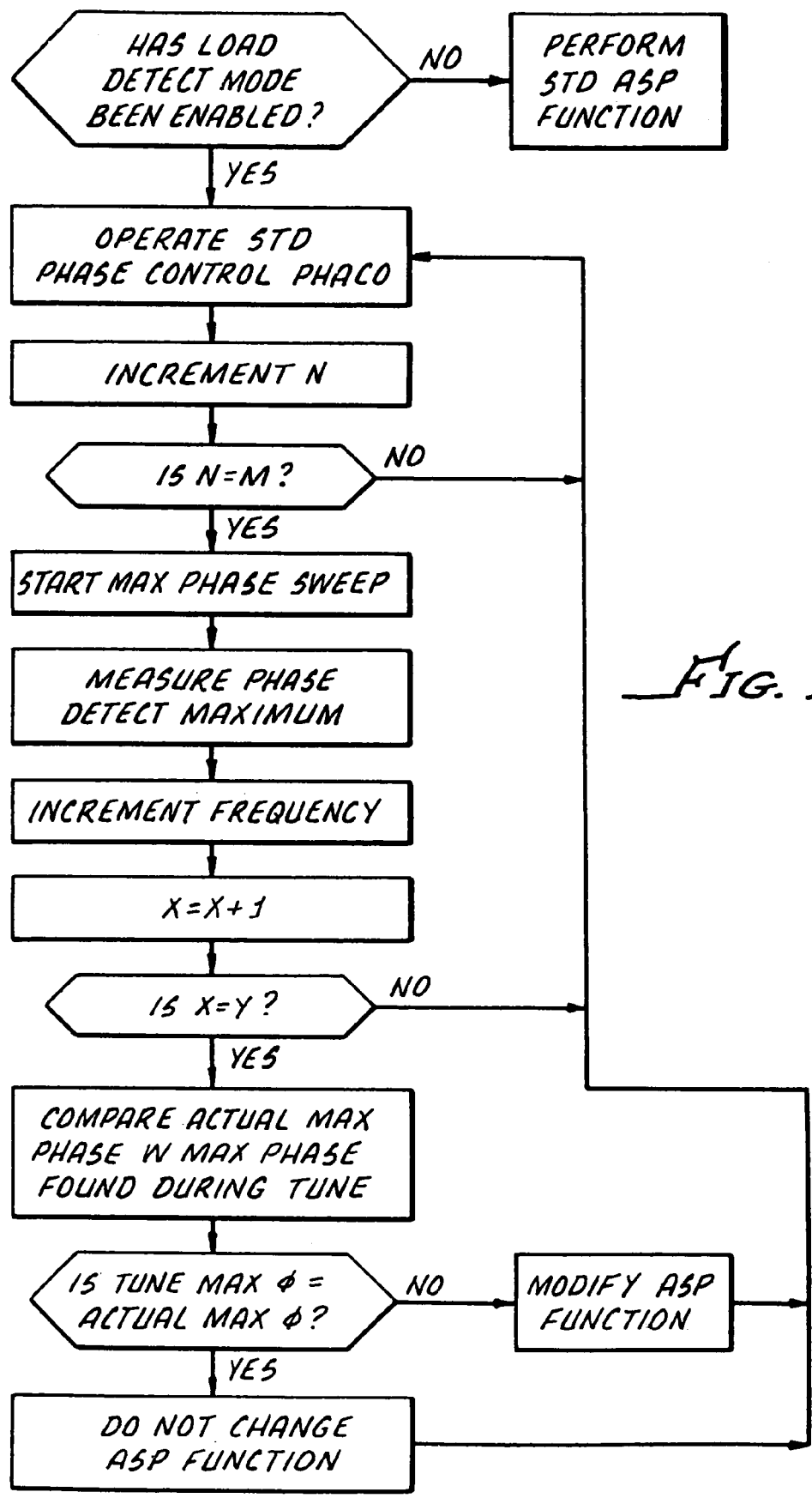
FIG. 13 is a function block control diagram of a phase control phacoemulsification system utilizing phase angles to control handpiece/needle parameters with a load detect method.

FIG. 13 represents operation at less than max load in which load (see FIG. 11) detection is incorporated into the operation, a method of the present invention.

As represented in FIG. 12, representing max phase mode operation, if the handpiece aspiration line 140 is occluded, the phase sensed by phase detector sensor 128 will decrease (see FIG. 11). The computer 118 has operator-settable limits for aspiration rates, vacuum levels and ultrasonic power levels. As illustrated in FIG. 12, when the phase sensed by phase detector 128 reaches a predetermined level as a result of occlusion of the handpiece aspiration line 140, computer 118 instructs pump speed controller 120 to change the speed of the peristaltic pump 114 which, in turn, changes the aspiration rate.

It will be appreciated that, depending upon the characteristics of the material occluding handpiece 40, the speed of the peristaltic pump 114 can either be increased or decreased. When the occluding material is broken up, the phase detector 128 registers an increase in phase angle, causing computer 118 to change the speed of peristaltic pump 114 to an unoccluded operating speed.

In addition to changing the phacoemulsification parameter of aspiration rate by varying the speed of the peristaltic pump 114, the power level and/or duty cycle of the ultrasonic power source 16 can be varied as a function of the occluded or unoccluded condition of handpiece 40.

Although there has been hereinabove described a method and apparatus for controlling a phacoemulsification handpiece utilizing the voltage current phase relationship of the piezoelectric phacoemulsification handpiece in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. Apparatus for the removal of lens tissue, said apparatus comprising:
    a first handpiece including a laser emitting probe sized for insertion into a lens capsule and radiating a lens therein;
    a second handpiece including a vibrated needle for insertion into said lens capsule and emulsifying lens tissue, said vibrated needle including a lumen therethrough for aspiration of emulsified lens tissue and irrigation fluid;
    a power source configured to provide pulsed electrical power to the second handpiece;
    an input configured to enable a surgeon to select an amplitude of the vibration of the needle; and
    a control console, in communication with the first handpiece and second handpiece and configured to control operation of the first handpiece and second handpiece and in response to the selected vibration amplitude for controlling a pulse duty cycle of power supplied to the second handpiece.

2. The apparatus according to claim 1 wherein said control console provides a pulse repetition rate of between 25 pulses per second and 2000 pulses per second to said second handpiece.

3. The apparatus according to claim 1 wherein said input enables a linear selection of pulse amplitude.

4. The apparatus according to claim 1 wherein said second handpiece includes a transducer for driving said vibrated needle at ultrasonic frequencies.

5. The apparatus according to claim 1 wherein said laser emitting probe comprises fiber optics.

6. A method for removing lens tissue from a lens capsule, said method comprising:
    inserting a laser emitting probe into said lens capsule;
    inserting a vibratable needle into said lens capsule;
    introducing irrigation fluid into said lens capsule;
    softening said lens tissue by exposure to laser energy from said laser emitting probe;
    vibrating the needle to emulsify softened lens tissue, wherein power provided to the needle for vibration is pulsed power having an amplitude and a pulse duty cycle;
    enabling a user to select the amplitude and pulse duty cycle of the pulsed power;
    controlling operation of the laser emitting probe and vibratable needle in order to effect emulsification of the lens tissue, wherein controlling the operation of the vibratable needle includes controlling the amplitude and the pulse duty cycle in response to the user's selection of amplitude and pulse duty cycle; and
    aspirating emulsified lens tissue and irrigation fluid from said lens capsule.

7. The method according to claim 6 wherein the needle is vibrated ultrasonically.

8. A method for removing lens tissue from a lens capsule, said method comprising:
    inserting a laser emitting probe into said lens capsule;
    inserting a vibratable needle into said lens capsule;
    introduction irrigation fluid into said lens capsule;

fracturing said lens tissue by exposure to laser energy from said laser emitting probe;

vibrating the needle to emulsify fractured lens tissue, wherein power provided to the needle for vibration is pulsed power having an amplitude and a pulse duty cycle;

enabling a user to select the amplitude and pulse duty cycle of the pulsed power;

controlling the fracturing of said lens tissue and emulsification of fractured lens tissue in order to effect emulsification of the lens tissue, wherein controlling the emulsification of the fractured lens includes controlling the amplitude and the pulse duty cycle in response to the user's selection of amplitude and pulse duty cycle; and aspirating emulsified lens tissue and irrigation fluid from said lens capsule.

9. The method according to claim 8 wherein the needle is vibrated ultrasonically.

10. The method according to claim 8 further comprising: controlling an off duty cycle to insure heat dissipation before a subsequent pulse is activated.

* * * * *